US005620683A

United States Patent [19]
Tong et al.

[11] Patent Number: 5,620,683
[45] Date of Patent: Apr. 15, 1997

[54] AQUEOUS, ACRYLIC HAIR FIXATIVES AND METHODS OF MAKING SAME

[75] Inventors: Quinn K. Tong, Belle Mead; Charles W. Paul, Madison, both of N.J.

[73] Assignee: National Starch and Chemical Investment Holding Corporation, Wilmington, Del.

[21] Appl. No.: 526,960

[22] Filed: Sep. 13, 1995

[51] Int. Cl.$^6$ ............................................. A61K 7/11
[52] U.S. Cl. ............................ 424/70.11; 424/70.16; 424/45; 424/47; 424/DIG. 1; 424/DIG. 2; 514/957; 132/202
[58] Field of Search .................. 424/45, 47, DIG. 1, 424/DIG. 2, 70.11, 70.16; 514/957; 132/202

[56] References Cited

U.S. PATENT DOCUMENTS

| | | | |
|---|---|---|---|
| 2,996,471 | 8/1961 | Reiter et al. | 260/33.4 |
| 3,574,822 | 4/1971 | Shepherd et al. | 424/47 |
| 3,660,561 | 5/1972 | Shepherd et al. | 424/47 |
| 3,810,977 | 5/1974 | Levine et al. | 424/47 |
| 3,927,199 | 12/1975 | Micchelli et al. | 424/47 |
| 4,192,861 | 3/1980 | Micchelli et al. | 424/47 |
| 4,196,190 | 4/1980 | Gehman et al. | 424/47 |
| 4,261,972 | 4/1981 | Nandagiri et al. | 424/47 |
| 4,315,910 | 2/1982 | Nowak, Jr. et al. | 424/47 |
| 4,798,721 | 1/1989 | Yahagi et al. | 424/70.11 |
| 4,842,852 | 6/1989 | Nowak, Jr. et al. | 424/70.11 |
| 4,961,921 | 10/1990 | Chuang et al. | 424/47 |
| 4,985,239 | 1/1991 | Yahagi et al. | 424/70.11 |
| 5,021,238 | 6/1991 | Martino et al. | 424/47 |
| 5,068,099 | 11/1991 | Sramek | 424/47 |
| 5,094,838 | 3/1992 | Benson et al. | 424/47 |
| 5,158,762 | 10/1992 | Pierce | 424/47 |
| 5,176,898 | 1/1993 | Goldberg et al. | 424/47 |
| 5,413,775 | 5/1995 | Hatfield et al. | 424/47 |

FOREIGN PATENT DOCUMENTS

| | | |
|---|---|---|
| 677267 | 9/1966 | Belgium . |
| 274086 | 7/1988 | European Pat. Off. . |
| 445714 | 9/1991 | European Pat. Off. . |
| 2697160 | 10/1992 | France . |
| 2098226 | 11/1982 | United Kingdom . |
| 2136689 | 9/1984 | United Kingdom . |
| 93/09757 | 5/1993 | WIPO . |
| 94/02112 | 2/1994 | WIPO . |

OTHER PUBLICATIONS

Oteri, R. et al. (1991). Cosmetics & Toiletries, vol. 106, pp. 29–34.

Martino, G. T. et al. (1992). Spray Technology & Marketing, Mar. issue, pp. 34–39.

Seifen–Ole–Fette–Wachse, vol. 117, No. 13, Aug. 28, 1991, pp. 464–467, J. Guth et al., "Addressing the North American Trend Toward Low VOC Hair Sprays".

*Primary Examiner*—Raj Bawa
*Attorney, Agent, or Firm*—William K. Wissing

[57] ABSTRACT

Aqueous, acrylic hair fixative compositions are disclosed which utilize a partially-neutralized acrylic hair fixative polymer. The polymer is neutralized in a solvent system in which water is always the major solvent constituent and organic solvents are optional. Methods of making the hair fixative compositions which require water as the primary solvent utilized to prepare the hair fixative compositions are also disclosed.

14 Claims, No Drawings

AQUEOUS, ACRYLIC HAIR FIXATIVES AND METHODS OF MAKING SAME

FIELD OF THE INVENTION

The present invention relates to aqueous hair fixative compositions which comprise a partially-neutralized, film-forming, acrylic polymer as a hair fixative resin and water as the primary solvent.

BACKGROUND OF THE INVENTION

In order to be effective in hair fixative compositions such as aerosol or nonaerosol hair sprays, mousses and lotions, the film forming resins utilized therein, as well as the films formed therefrom, must meet certain requirements. The resins used in such compositions should be soluble in the solvent systems used to prepare the hair fixative compositions. Particularly in hair fixative compositions containing low levels of volatile organic compounds (VOC), where water is used as the primary solvent, the resin should be water-soluble in order to prepare aqueous solutions of the resins. The resins also must be compatible with the solvent/propellant system in the aerosol applications in order to provide the aerosol fixatives with adequate spray properties. In addition, the films cast from such compositions must be either water-soluble or water-dispersible in order to facilitate the easy removal from the user's hair.

One class of resins used in hair fixatives are acrylic polymers which contain carboxylic acid groups. Exemplary of such acrylic polymer resins containing carboxylic acid groups include without limitation the copolymers of n-tert-octylacrylamide, methyl methacrylate, hydroxypropyl methacrylate, acrylic acid and t-butyl aminoethyl methacrylate, available from National Starch and Chemical Company under the Amphomer and the Amphomer LV-71 trade names; copolymers of n-tertoctylacrylamide, methyl methacrylate, acrylic acid and t-butyl aminoethyl methacrylate, available from National Starch and Chemical Company under the Lovocryl trade name; and copolymers of vinyl acetate, crotonic acid and a vinyl ester of an alpha-branched saturated aliphatic monocarboxylic acid containing from 5 to 10 carbon atoms in the carboxylic acid moiety, available from National Starch and Chemical Company under the Resyn trade name.

Such acrylic copolymers are known to be soluble in organic solvents such as ethanol and, thus, typically are used in hair fixative compositions which utilize an organic solvent as the sole or primary solvent. Such acrylic polymers, it is suggested, are known not to be water-soluble unless their carboxylic acid groups are neutralized by alkaline reagents to a level of at least 90% on a molar basis. If the neutralization on a molar basis is lower than 90%, the films derived from those hair fixative compositions utilizing the acrylic polymers generally should not be water-soluble and the fixative resins should not be removable readily from the hair. Accordingly, if such acrylic polymers are intended to be used in formulating low VOC hair fixative compositions, it is taught generally to neutralize the carboxylic acid content to at least 90 mole percent to enhance the water-solubility of the resin and to ensure the easy removal of the resin from the hair. For example, in International Publication No. WO/93/09757, in hair fixative compositions containing water as the primary solvent and a propellant, 100 mole percent of the carboxylic functionality on the acrylic polymers are neutralized.

In addition to being removable readily from the hair, the resin also must be compatible with the solvent/propellant system. The general water-insolubility of such acrylic polymers creates specific problems with respect to hair fixative compositions which contain water as the sole or primary solvent and a propellant, under pressure, such as low VOC aerosol sprays. In such aerosol hair spray applications, a uniform, fine mist or spray is desirable to effectively distribute the hair fixative on the hair. The high levels of neutralization required to provide solubility of the resin in water and thereby removability of the film from hair, results in increased viscosity of the hair fixative compositions. The high viscosity results in undesirable spray aesthetics, such as a narrow spray cone, large spray droplets, spitting, foaming and forceful spray, for example. Therefore, as indicated above, the carboxylic acid functionality of the acrylic polymers are neutralized prior to their incorporation into such low VOC hair fixatives, generally at a level from 90% to 100% on a molar basis.

Neutralization methods are generally known where such acrylic polymers are neutralized prior to be used in hair fixative compositions. Particularly, U.S. Pat. No. 3,927,199 discloses hair fixative compositions containing acrylic copolymers and organic solvent as the primary solvent. In order to meet the removability requirement of a hair fixative, the acrylic resins may be partially neutralized prior to their being incorporated into the hair fixing formulations, thus permitting them to be removed from the hair merely be rinsing with water. The neutralization may be accomplished by reacting the polymer in the form of a solution in an organic solvent, with or without added water, with a concentration of an alkaline reagent (neutralizing agent) which is equivalent on a molar basis to a minimum of about 50% of the available carboxyl groups present on the polymer. The above method can be conducted in the presence of organic solvents such as ethanol. Methods of neutralizing the acrylic polymer in water as the primary solvent are not disclosed or discussed.

U.S. Pat. No. 4,315,910 discloses acrylic polymers for use in aerosol hair fixatives. Small amounts of water, i.e., 1 to 15%, preferably 3 to 8%, are taught to improve the shelf stability and solubility of the polymer. The carboxylic acid groups of the copolymer require neutralization to enhance the water-solubility of the resin to ensure the easy removal of the resin from the hair. The neutralization of acrylic polymers is accomplished by first reacting a solution of the polymer in an organic solvent, with or without added water, with a concentration of an alkaline reagent which is effective to neutralize 70 to 100 mole percent of the carboxyl groups. The appropriate amount of water (not to exceed 15% w/w) is added then to the organic solvent solution of the neutralized resin prior to charging the formulation into the aerosol container. The propellant used in the aerosol applications is a hydrocarbon or carbon dioxide.

U.S. Pat. No. 4,261,972 discloses pressurized hair spray compositions which may contain a broad range of acrylic resin hair fixatives and from 2 to 30% by weight of water. The acid groups of the acrylic resins are neutralized from 50 to 100 percent with an organic base. When the water content is above 30%, the product is dispensed as a foam, which is not desired. The propellants used in these aerosol applications are hydrocarbons.

There has been an ongoing effort in the hair care industry to significantly reduce or eliminate organic solvents in hair fixatives. Additionally, regulatory bodies push to lower the level of VOC, which include ethanol and equivalent hair fixative solvents, in various industries, including hair care products. As the art suggests, increased levels of water, i.e., up to 30 weight percent, are sought to correct certain deficiencies of organic solvent systems, such as flammability and plasticization.

While the methods of neutralization noted above may be used where an organic solvent is the primary or sole solvent, neutralization where water is the primary or sole solvent used to prepare the hair fixatives is problematic. In the known methods, the dry acrylic polymer is dissolved in the organic solvent prior to being incorporated into the hair fixative, which may include small amounts of water blended therein. However, where water is the primary solvent, one must first determine how to dissolve the water-insoluble, unneutralized polymer in the water solvent. Thus, methods of preparing hair fixative compositions which significantly reduce or eliminate organic solvents in the hair fixative compositions are sought.

The present invention provides such methods for preparing low VOC, acrylic hair fixative compositions, which methods significantly reduce or eliminate organic solvents from methods for making the hair fixatives and the hair fixatives produced therefrom.

SUMMARY OF THE INVENTION

The present invention is directed to methods for preparing aqueous, acrylic, hair fixative compositions. The method comprises combining to a total of 100 weight percent, about 3 to 10 weight percent of an acrylic hair fixative polymer comprising from about 8 to about 25 weight percent of the residue of an acidic monomer which contains at least one carboxyl group, based on the total weight of monomer used to prepare the polymer, 25 to 97 weight percent of water, 0 to 40 weight percent of a propellant, an amount of a neutralizing agent effective to neutralize from 40 to 80 mole percent of the carboxylic acid groups present in the polymer, 0 to 15 weight percent of an emulsifier and 0 to 35 weight percent of an organic solvent; under conditions effective to form an aqueous, homogenous solution of the polymer in the water, thereby forming an aqueous, acrylic, hair fixative composition, wherein the water is the primary solvent used in preparing the hair fixative composition. The invention is also directed to aqueous, acrylic, hair fixative compositions prepared by the methods of the present invention.

DETAILED DESCRIPTION OF THE INVENTION

Acrylic polymer, as used herein, is intended to include those polymers which contain at least one $\alpha$-$\beta$ ethylenically unsaturated acidic monomer containing one or more carboxylic groups. Preferred acrylic, film forming polymers utilized as resins in the hair fixative compositions of this invention comprise polymers containing the residue of at least one acidic monomer containing one or more carboxyl groups, and at least one monomer selected from a group of monomers which are copolymerizable with the acidic monomers, hereinafter referred to as a copolymerizable monomer.

The following list of monomers are representative of the applicable acrylic, acidic film forming monomers which contain at least one carboxylic acid group: acrylic acid, methacrylic acid, crotonic acid, itaconic acid, maleic acid, fumaric acid and the $C_1$–$C_4$ alkyl half esters of maleic and fumaric acids, such as methyl hydrogen maleate and butyl hydrogen fumarate, as well as any other acidic monomers which are capable of being copolymerized with the particular polymer system whose use is desired by the practitioner.

As is known to those skilled in the art, the acidic monomer must be chosen so as to be readily polymerizable with the selected polymer system.

In order to modify or enhance certain properties of the polymeric binder, for example, adherence to the hair, water-solubility, hardness, flexibility, antistatic properties, and the like, the practitioner may utilize one or more copolymerizable monomer in the preparation of the polymeric resins of this invention. Among these copolymerizable monomers are the acrylic and methacrylic acid esters of aliphatic alcohols having from 1 to 12 carbon atoms such as methyl, ethyl, propyl, butyl, octyl and lauryl alcohols; hydroxyalkyl esters of acrylic and methacrylic acids such as hydroxypropyl acrylate and methacrylate, hydroxybutyl acrylate and methacrylate, hydroxystearyl acrylate and methacrylate and hydroxyethyl acrylate and methacrylate; alkyl ($C_1$–$C_4$) amino alkyl ($C_2$–$C_4$) esters of acrylic and methacrylic acids such as N, N'-dimethylaminoethyl methacrylate, N-tert-butylaminoethyl methacrylate and the quaternization product of dimethylaminoethyl methacrylate and dimethyl sulfate, diethyl sulfate and the like; diacetone acrylamide; vinyl esters such as vinyl acetate, vinyl neodecanoate and vinyl propionate; and styrene monomers such as styrene and alpha-methyl styrene, and N-substituted acrylamides or methacrylamides substituted with alkyl radicals containing from 2 to 12 carbon atoms. Among the applicable acrylamides and methacrylamides are included N-ethyl acrylamide, N-tertiary-butyl acrylamide, N-n-octyl acrylamide, N-tertiary-octyl acrylamide, N-decyl acrylamide, N-dodecyl acrylamide, as well as the corresponding methacrylamides.

In order to provide resins which will function efficiently in the novel hair fixative compositions of this invention, the polymer may comprise the residue of from about 0 to 60% of the N-substituted acrylamide or methacrylamide, from 8 to 25%, of the acidic monomer, and 0 to 90% of at least one copolymerizable monomer other than the N-substituted acrylamide or methacrylamide. Preferably, the polymer comprises the residue of from about 10 to 22 percent of the acidic monomer, from about 35 to 55 percent of the N-alkyl acrylamide or methacrylamide monomer and from about 25 to 80 percent of the copolymerizable monomer other than the N-substituted acrylamide or methacrylamide. Most preferably, the polymer comprises the residue of from about 15 to 20 percent of the acid monomer, 38 to 52 percent of the N-alkylacrylamide or methacrylamide and 30 to 50 percent of the copolymerizable monomer, all weights based on the total weight of monomers used to prepare the polymers.

As for the actual preparation of these polymeric film forming resins, there may be employed any of the usual vinyl polymerization methods which are well known to those skilled in the art and which are particularly suited for the polymer whose preparation is desired. Thus, the polymers may be prepared by means of free radical initiated processes utilizing bulk, suspension, solution, or emulsion polymerization techniques. The polymers may, if desired, be converted into relatively large particles known as beads or pearls by dispersing the solution polymerized polymer in water and thereafter driving off the solvent followed by separating and drying the particles.

The polymer resins of this invention are partially neutralized in a solvent system where water is the primary solvent, with an amount of an alkaline reagent (neutralizing agent) which is equivalent on a molar basis to from about 40 to 80 percent of the carboxyl groups present on the polymer. Applicable alkaline materials which may be utilized in this manner include sodium and potassium hydroxide, ammonia, primary, secondary and tertiary amines, alkanolamines and, hydroxyamines such as 2-amino-2-methyl-propanol and 2-amino-2-methyl-1,3-propanediol.

In preparing the hair fixative compositions of the present invention, the polymer, typically in powder form, is combined with a solvent system, or with a solvent/propellant system, and an amount of a neutralizing agent which is effective to neutralize from about 40 to about 80 mole percent of the carboxylic groups in the polymer, under conditions effective to form an aqueous, homogeneous solution of the polymer in the solvent system or the solvent/propellant system. The solution must be stable from phase separation and precipitation and most preferably forms clear, continuous films which are redispersible in water, i.e., removable from hair readily with water. Preferably, the viscosity of the solution of polymer in the solvent/propellant system will be sufficient to provide the spray properties required of aerosol hair fixatives.

The solvent system comprises water as the primary solvent. The hair fixative compositions contain from 25 to about 97 weight percent of water and may consist essentially of the water, the neutralizing agent and the polymer. In other embodiments, the hair fixative compositions will comprise from about 25 to about 77 weight percent water, more preferably from about 35 to 65 weight percent water. The solvent system may further include organic solvents such as ethanol, isopropanol, acetone, dimethoxymethane and methyl ethyl ketone. By primary solvent, it is meant that water is always the major constituent of the solvent system. That is to say, water always comprises greater than 50 weight percent of the solvent system, preferably greater than 60 weight percent and even more preferably greater than about 75 weight percent of the solvent system. The organic solvents may be used at levels up to 35 weight percent, based on the total weight of the hair fixative composition. Preferably not more than 25 weight percent of the organic solvent is used. In certain embodiments, it is desired that water be the sole solvent used to prepare the hair fixative compositions.

The hair fixative compositions may be in the form of an aerosol or non-aerosol spray, a mousse or a hair-setting lotion. The compositions may contain up to 40 weight percent, preferably up to 35 weight percent, of propellants. In aerosol spray hair fixative compositions, it is preferably to use from about 25 to about 35 weight percent of a propellant. Typical propellants include ethers, compressed gases, halogenated hydrocarbons and hydrocarbons. Exemplary propellants are dimethyl ether, compressed nitrogen, air or carbon dioxide, propane, butane and 1,1-difluoroethane. The compositions may further include other materials or additives such as fragrances, preservatives, colorants, plasticizers, emulsifiers, conditioners, neutralizers, glossifiers and the like. Such propellants, organic solvents and materials or additives are commonly used in hair fixative compositions known heretofore.

In preparing the hair fixative compositions according to the present invention, The acrylic polymer is neutralized to the extent that from about 40 to 80 mole percent of the carboxylic groups in the acrylic polymer are neutralized by the neutralization agent, in a solvent system wherein water is the primary solvent. Neutralization below about 40 mole percent results in settling, precipitation or phase separation of the polymer from the solvent system. Neutralization to greater than about 80 mole percent results in high solution viscosities, both solutions of the polymer in the solvent system and the solution of the polymer in a solvent/propellant system, which detrimentally affect the spray characteristics and properties of aerosol hair fixatives which utilize the partially-neutralized acrylic polymers of the present invention. Preferably, the acrylic polymers are neutralized to from about 50 to about 75 mole percent. It is particularly preferred that the polymers contain from about 6 to about 20 mole percent of neutralized carboxylic groups, more preferably from about 8 to about 16 mole percent.

In methods of preparing the hair fixative compositions, the neutralization agent is added to the water in predetermined amounts to neutralize a predetermined amount of carboxylic groups (40 to 80 mole percent) present in the polymer. The polymer is then added to the mixture of the water and neutralization agent with stirring to form a slurry of the polymer in the aqueous mixture. In certain embodiments, the polymer slurry is heated to a temperature and for a time effective to form an aqueous, homogenous solution of the polymer in the solvent system, which comprises primarily water as the solvent. Depending on the specific polymer, the degree of neutralization and the solvent system, the temperature to which the slurry is heated may range from about 70° C. to about 80° C. and the period of time over which the temperature is maintained may vary from a few minutes, i.e., 5 to 10 minutes, to a period of hours, i.e., 1 to 3 hours. Temperatures are preferably selected to minimize the time period. Upon heating under such conditions, the aqueous, homogenous polymer solution is formed. The aqueous polymer solution then may be combined with the optional ingredients, such as the organic solvent, the propellant, and the emulsifier. Where a propellant is used, the mixture is pressurized under according to conventional standards to form an aqueous, acrylic, aerosol hair fixative, such as a hair spray and an aerosol mousse where an emulsifier is present.

In other methods of preparing the hair fixatives, the propellant is combined with the polymer slurry under conditions effective to form an aqueous, homogenous solution of the polymer in the solvent/propellant system. Pressures utilized are those conventionally used to prepare aerosol sprays and mousses, such as from about 40 psi to about 63 psi. It has been discovered that by simply combining the polymer, neutralization agent, water and propellant and, optionally the organic solvent and emulsifier, under such pressures and without any heating, the slurry/propellant system became clear and homogenous within about 24 to 72 hours under storage at ambient temperatures.

Mousses according to the present invention further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation—Nonoxynol 15) and Brij 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water. Optional additives may be incorporated into the hair fixing formulations of this invention in order to modify certain properties thereof. Among these additives may be included plasticizers such as glycols, phthalate esters and glycerine; silicones; emollients, lubricants and penetrants such as lanolin compounds, protein hydrolyzates and other protein derivatives, ethylene oxide adducts, and polyoxyethylene cholesterol; U.V. absorbers; dyes and other colorants; and, perfumes. As previously noted, the polymeric resins of this invention show little or no tendency to chemically interact with such additives.

The resulting hair fixing formulations exhibit all of the characteristics required of such a product. Their films are transparent, glossy, and continuous. They possess good antistatic properties, adhere well to hair, are easily removed by soapy water or shampoos, allow the air to be readily recombed, do not yellow on aging, do not become tacky when exposed to high humidities, and have excellent curl retention under high humidity conditions.

The following examples are not intended to and should not be construed to limit the scope of the invention, the scope of which is limited only by the claims appended hereto.

POLYMER PREPARATION

A series of acrylic polymers comprising the residue of from about 15 to 20 percent of acrylic acid monomer, 40 to 50 percent of a N-alkyl acrylamide monomer and about 30 to 50 percent of a mixture of copolymerizable monomers other than the N-alkyl acrylamide monomer was prepared utilizing standard precipitation polymerization techniques known to those skilled in the art. The polymer powders so prepared were designated Polymers 1A (16% AA), 1B and 1C (both 20% AA), respectively. All percentages of monomers herein are based on the total weight of monomers used to prepare the polymers.

An acrylic polymer comprising the residue of about 10 percent of crotonic acid and 90 percent of a mixture of vinyl ester monomers was prepared similarly to Polymer 1A and designated Polymer 1D.

The polymers were neutralized as described below and formulated into hair fixative compositions comprising the neutralized polymer, a solvent system and, optionally, a propellant or propellant analogue. The hair fixatives were evaluated as described below for various properties which are critical in formulating hair fixatives, especially aerosol fixatives, such as clarity and or homogeneity in the solvent or solvent/propellant system, viscosity in the solvent or solvent/propellant system and film characteristics such as clarity, continuity, i.e., cracking and redispersibility in water, i.e., removability from hair.

Evaluation Protocol

Appearance of Polymer in Solvent System or Solvent/Propellant System:

The appearance of the neutralized polymer in either the solvent system of the solvent/propellant system was visually evaluated for clarity and for homogeneity. Solutions which were hazy to clear and which exhibit no cloudiness, settling, precipitation or phase separation were considered to be viable candidates for hair fixative compositions of the present invention.

Evaluation of Films

Film Appearance:

1.5 ml of the aqueous, homogenous polymer solution (5 weight percent polymer) was placed into a tin receptacle and dried overnight in a constant temperature/humidity chamber set at 50% relative humidity to form a film. The receptacles were place on dry ice to effect removal of the film from the receptacle. The films were visually observed for signs of cracks or other incontinuities of the film.

Redispersibility in Water:

Prescreening shampoo removability of partially-neutralized polymers was conducted by placing the film formed from the polymer solution into about 15 ml of polished water without heating or agitation. Generally, if the film is soluble in water, the film first becomes swollen, becomes gel-like in the water, and finally dissolves in the water. Polymers considered to be successful candidates for hair fixatives according to the present invention typically will dissolve within 1 to 2 minutes after being placed in the water. Films which do not dissolve in the water are not considered to be viable resins for the hair fixatives of the present invention.

Solution Viscosity:

The viscosity of the solutions of the polymer in the solvent/propellant system was measured at 25° C., using a Cannon Capillary Viscometer, having a range of from 0 to 50 cps.

EXAMPLE 1

Neutralization of Polymer in Ethanol

Polymers 1A and 1B each were dissolved in ethanol at a level of 7.5 weight percent, based on the total weight of the polymer and ethanol. The carboxylic groups of each polymer were neutralized under ambient conditions of pressure and temperature to various levels with 2-amino-2-methyl propanol, as indicated in Table 1. Films were cast from each solution and evaluated for film appearance and redispersibility in water. As indicated in Table 1, films formed from each solution were clear and continuous, meaning that no cracks in the films were noted. However, films cast from the solutions of Polymer 1A were not redispersible in water at either 70% or 80% neutralization. All percentages of neutralization herein indicate the mole percent of carboxylic groups present in the polymer which have been neutralized. Those films cast from solutions of Polymer 1B were not redispersible in water at 70% neutralization or less and were soluble at 90% neutralization. At 80% neutralization, the films are redispersible in water, although dissolution is slow.

TABLE 1

| POLYMER | NEUTRALIZATION Mole % | FILM APPEARANCE | FILM REDISPERSIBILITY IN $H_2O$ |
|---|---|---|---|
| 1A | 70 | CLEAR, CONTINUOUS | NO |
| 1A | 80 | CLEAR, CONTINUOUS | NO |
| 1B | 50 | CLEAR, CONTINUOUS | NO |
| 1B | 60 | CLEAR, CONTINUOUS | NO |
| 1B | 70 | CLEAR, CONTINUOUS | NO |
| 1B | 80 | CLEAR, CONTINUOUS | SLOWLY |
| 1B | 90 | CLEAR, CONTINUOUS | YES |

EXAMPLE 2

Neutralization of Polymer in Water

Polymer 1A was neutralized in water to various levels by combining the polymer, at a level of 5 weight percent, with a blend of water and 2-amino-2-methyl propanol (neutralizing base), thereby forming a slurry of the polymer powder in the water/base blend. The level of 2-amino-2-methyl propanol was varied such that the carboxyl groups on the polymer were neutralized to from 20% to 90%. The slurry was heated to about 70° C. until such time as a homogeneous solution of the polymer in water was formed. Where such homogenous solutions were formed, films were cast therefrom and evaluated for film appearance and film redispersibility in water.

Polymer 1A was neutralized in water/ethyleneglycol dimethyl ether (DME*—a liquid analogue of dimethyl ether) to various levels by combining the polymer, at a level of 5 weight percent, with a blend of water and 2-amino-2-methyl propanol, thereby forming a slurry of the polymer powder in the water/base blend. The level of 2-amino-2-methyl propanol was varied such that the carboxyl groups on the polymer were neutralized to from 20% to 90%. An appropriate amount of the DME* was added to the polymer slurry under ambient conditions of pressure and temperature. Where homogeneous solutions of the polymer in the water/DME* blends were formed, films were cast therefrom and evaluated for film appearance and film redispersibility in water.

As the data indicates, neutralization of the carboxylic groups to less than about 40 mole percent results in cloudiness and settling or separation in either water or water/DME*. Furthermore, at about 40 mole percent neutralization, the films start to exhibit signs of cracking and marginal redispersibility in water. The data also indicates that the viscosity in water/DME* increases with increased neutralization of the carboxylic groups. The increase in viscosity becomes a critical factor in the formulation of aerosol hair fixatives, where spray aesthetics and properties are of concern.

TABLE 2A

| NEUTRA-LIZATION MOLE % | APPEARANCE IN SOLVENT | APPEARANCE IN SOLVENT/DME* | VISCOSITY IN SOLVENT/DME* (cP) | APPEARANCE OF FILM | FILM REDISPERSIBILITY IN H$_2$O |
|---|---|---|---|---|---|
| 90 | CLEAR | CLEAR | 10.70 | CLEAR | YES |
| 80 | CLEAR | CLEAR | 9.15 | CLEAR | YES |
| 70 | CLEAR | CLEAR | 7.44 | CLEAR | YES |
| 60 | CLEAR | CLEAR | 6.06 | CLEAR | YES |
| 50 | SL. HAZY | CLEAR | 5.07 | CLEAR | YES |
| 40 | HAZY | HAZY | 4.38 | HAZY, CRACKS | NOT FULLY |
| 35 | CLOUDY SETTLED | HAZY SETTLED | — | — | — |
| 30 | CLOUDY, SETTLING | CLOUDY, TWO LAYERS | — | — | — |
| 20 | CLOUDY, SETTLING | — | — | — | — |

Polymers 2B and 2C were neutralized and evaluated in the same manner as Polymer 1A above. Results are set forth in Table 2B and 2C, respectively.

TABLE 2B

| NEUTRA-LIZATION MOLE % | APPEARANCE IN SOLVENT | APPEARANCE IN SOLVENT/DME* | VISCOSITY IN SOLVENT/DME* (cP) | APPEARANCE OF FILM | FILM REDISPERSIBILITY IN H$_2$O |
|---|---|---|---|---|---|
| 90 | CLEAR | CLEAR | 11.97 | CLEAR | YES |
| 80 | CLEAR | CLEAR | 10.46 | CLEAR | YES |
| 70 | CLEAR | CLEAR | 8.71 | CLEAR | YES |
| 60 | CLEAR | CLEAR | 7.07 | CLEAR | YES |
| 50 | CLEAR | CLEAR | 6.09 | CLEAR | YES |
| 40 | CLEAR | CLEAR | 4.90 | CLEAR | NOT FULLY |
| 30 | CLOUDY | HAZY | 4.10 | — | — |
| 20 | CLOUDY, PRECIPITATE | — | — | — | — |

TABLE 2C

| NEUTRA-LIZATION MOLE % | APPEARANCE IN SOLVENT | APPEARANCE IN SOLVENT/DME* | VISCOSITY IN SOLVENT/DME* (cP) | APPEARANCE OF FILM | FILM REDISPERS-IBILITY IN H$_2$O |
|---|---|---|---|---|---|
| 90 | CLEAR | CLEAR | 4.29 | CLEAR | YES |
| 80 | CLEAR | CLEAR | 4.10 | CLEAR | YES |
| 70 | CLEAR | SL. HAZY | 3.90 | CLEAR | YES |
| 60 | CLEAR | HAZY | 3.66 | CLEAR | YES |
| 50 | CLEAR | HAZY | 3.514 | CLEAR | YES |
| 40 | HAZY | HAZY | 3.18 | CLEAR | NOT FULLY |
| 30 | CLOUDY, SETTLED | CLOUDY | 2.97 | — | — |
| 20 | | — | | — | — |

EXAMPLE 3

Effects of Organic Solvent in Solvent System

In order to determine the effects of including an organic solvent in the solvent system utilized in formulating the hair fixative compositions of the invention, Polymer 1A (5% by weight) was neutralized as above both in the presence of ethanol and water and in the presence of ethanol, water and DME*. The solutions formed from the polymer and the solvent system or from the polymer and the solvent/propellant systems were evaluated for appearance. Films cast from the various solutions were evaluated for appearance and redispersibility in water. Results are set forth in Table 3A. As the results indicate, where ethanol is present in amounts of 35 weight percent or more, the films formed therefrom are not redispersible in water. Additionally, an increase in the viscosity of the solution of the polymer in the solvent/propellant system increases with the increased level of ethanol. Accordingly, organic solvent is limited to about 35 weight percent or less.

Solutions and the films formed therefrom were evaluated as above. Results are set forth in Table 4.

TABLE 3A

| ETHANOL (wt. %) | APPEARANCE IN SOLVENT | APPEARANCE IN SOLVENT/DME* | VISCOSITY IN SOLVENT/DME* (cP) | APPEARANCE OF FILM | FILM REDISPERSI-BILITY IN H$_2$O |
|---|---|---|---|---|---|
| 0 | SL. HAZY | CLEAR | 5.07 | CLEAR | YES |
| 5 | CLEAR | CLEAR | 5.97 | CLEAR CRACKS | YES |
| 15 | CLEAR | CLEAR | 8.20 | CLEAR, CONTINUOUS | YES |
| 25 | CLEAR | CLEAR | 10.57 | CLEAR, CONTINUOUS | YES |
| 35 (Added before water) | — | CLEAR | 8.84 | CLEAR, RUBBERY | NO, SWOLLEN |
| 35 (Added into water-polymer) | CLEAR | CLEAR | — | CLEAR, RUBBERY | NO, SWOLLEN |
| 70 (No water added) | — | CLEAR | — | CLEAR, CONTINUOUS | NO, SWOLLEN |

EXAMPLE 4

Neutralization Agents

Polymers 1A, 1B and 1C (5% by weight) were neutralized at levels and with neutralization agents as noted in Table 4, and under conditions similar to those set forth in Example 2.

TABLE 4

| POLY-MER | NEUTRALIZATION AGENT | NEUTRALIZATION MOLE % | APPEARANCE IN SOLVENT | APPEARANCE IN SOLVENT/DME* | VISCOSITY IN SOLVENT/DME* (cP) |
|---|---|---|---|---|---|
| 1A | AMP | 50% | CLEAR | CLEAR | 5.07 |
| 1B | AMP | 50% | CLEAR | CLEAR | 6.35 |
| 1C | AMP | 70% | CLEAR | HAZY | 3.90 |
| 1A | AMP/NaOH (50/50 w/w) | 50% | CLEAR | CLEAR | 5.32 |
| 1A | AMP/DMSA (75/25 w/w) | 50% | HAZY | HAZY | 4.68 |
| 1C | AMP | 60% | CLEAR | SLIGHTLY HAZY | 5.94 |

AMP - 2-amino-2-methyl propanol
NaOH - sodium hydroxide
DMSA - dimethyl stearic amine

EXAMPLE 5

Polymer 1D (5% by weight) was neutralized to 50% in the presence of water and ethanol and in the presence of water, ethanol and DME*. Where the polymer and ethanol were combined prior to being combined with the water and base, homogenous solutions were prepared with no heating. Where the ethanol was added to the slurry of the polymer and water/base, homogenous solutions were not formed, indicating that the slurry should be heated to form a homogenous solution of the polymer in water prior to adding the organic solvent to the polymer/water slurry. At 50% neutralization, the films formed from the solutions were not redispersible in water, indicating that higher levels of neutralization are desired for polymers similar to Polymer 1D. See Table 5A.

Polymer 1D (5% by weight) was neutralized to 80% as noted below and evaluated for appearance in the solvent system and in the solvent/propellant system.

In the first case, Polymer (5%), water (balance to 100%), 2-amino-2-methyl propanol (80% neutralization) and ethanol (15%) were combined as follows. The polymer, water and base were heated as herein above in order to form a homogenous, aqueous polymer solution. The ethanol was added to the aqueous, polymer solution and films cast from the solutions were evaluated as above. In the second case, the water, base, polymer, ethanol and DME* were combined for a time sufficient to form a homogenous solution of the polymer in the solvent/propellant system. The solutions and films were evaluated as above. See Table 5A.

TABLE 5A

| ETHANOL (wt. %) | APPEARANCE IN SOLVENT | APPEARANCE IN SOLVENT/DME* | VISCOSITY IN SOLVENT/DME* (cP) | APPEARANCE OF FILM | FILM REDISPERSI-BILITY IN H₂O |
|---|---|---|---|---|---|
| 5 | Not homogeneous solution Heating required | — | — | — | — |
| 20 (Added before water) | Cloudy No heating required | Cloudy | 6.07 | Cloudy | No Swollen |
| 20 (Added into water-polymer) | Not homogeneous solution Heating required | — | — | — | — |
| 35 (Added before water) | Clear No heating required | Clear | 5.29 | Clear | No Swollen |
| 35 (Added into water-polymer) | Clear Heating required | Clear | 5.67 | Clear | No Swollen |
| 67 (No water added) | Clear No heating required | Clear | 2.12 | Clear | No Swollen |

In the third case, the polymer (5%) and the ethanol (20%) were combined. The water/base blend was added to the polymer/ethanol, and a homogenous solution was formed. In the fourth case, the water, base, polymer, ethanol and DME* were combined for a time sufficient to form a homogenous solution of the polymer in the solvent/propellant system. The solutions and films were evaluated as above. See Table 5B.

TABLE 5B

| ETHANOL (wt. %) | | APPEARANCE IN SOLVENT | APPEARANCE IN SOLVENT/DME* | VISCOSITY IN SOLVENT/DME* (cP) | APPEARANCE OF FILM | FILM REDISPERS-IBILITY IN $H_2O$ |
|---|---|---|---|---|---|---|
| 15 (Added into water-polymer) | 1) 2) | Polymer-water Heating required Add EtOH | Cloudy | 6.98 | Clear | Yes |
| 20 (Added before water) | 1) 2) | Polymer-EtOH Add $H_2O$ No heating required | Slightly hazy | 6.99 | Clear | Yes |

We claim:

1. An aqueous, acrylic, hair fixative composition, comprising to a total of 100 percent by weight, about 3 to 10 weight percent of an acrylic hair fixative polymer which has been prepared utilizing from about 8 to about 25 weight percent of an acidic monomer which contains at least one carboxyl group and which is selected from the group consisting of acrylic acid, methacrylic acid, crotonic acid, itaconic acid, maleic acid, fumaric acid, $C_1$–$C_4$ alkyl half esters of maleic acid and $C_1$–$C_4$ alkyl half esters of fumaric acid, based on the total weight of monomer used to prepare the polymer, 25 to 97 weight percent of water, 0 to 40 weight percent of a propellant, an amount of a neutralizing agent effective to neutralize from 40 to 80 mole percent of the carboxyl groups present in the polymer, 0 to 15 weight percent of an emulsifier; and 0 to 35 weight percent of an organic solvent;

characterized in that the polymer, the water, and the neutralizing agent are combined for a time period ranging from about 5 minutes to about 72 hours, at a temperature and a pressure ranging from standard temperature and pressure to a temperature of about 80° C. and a pressure of about 63 psi, thereby forming an aqueous, homogenous solution of the polymer in the water, wherein the water comprises greater than 50 weight percent of a solvent system which comprises the water and optionally the organic solvent, which solvent system is used in preparing the hair fixative composition.

2. The composition of claim 1 wherein the polymer, the water and the neutralizing agent are combined and heated at a temperature ranging from about 70° C. to about 80° C. and for a period of time ranging from about 5 minutes to about 3 hours, thereby forming the aqueous, homogenous solution of the polymer.

3. The composition of claim 1 wherein the polymer, the water and the neutralizing agent are heated to a temperature of from about 70° C. to about 80° C. until the aqueous, homogeneous solution is formed.

4. The composition of claim 2 wherein the aqueous, homogeneous solution of the polymer and from 2.5 to 35 weight percent of the propellant are combined under pressures ranging from about 40 psi to about 63 psi, thereby forming the hair fixative composition.

5. The composition of claim 1 wherein the polymer, the water, the neutralizing agent and 25 to 35 weight percent of the propellant are combined at standard temperature, under pressures ranging from about 40 psi to about 63 psi and for a period of time ranging from about 24 hours to about 72 hours, thereby forming the aqueous, acrylic, aerosol hair fixative composition.

6. The composition of claim 1 comprising less than 25 weight percent of the organic solvent.

7. The composition of claim 1 comprising from about 35 to about 65 weight percent of the water and less than 25 weight percent of the organic solvent.

8. A method for preparing an aqueous, acrylic, hair fixative composition, comprising:

combining to a total of 100 percent by weight, about 3 to 10 weight percent of an acrylic hair fixative polymer which has been prepared utilizing from about 8 to about 25 weight percent of an acidic monomer which contains at least one carboxyl group and which is selected from the group consisting of acrylic acid, methacrylic acid, crotonic acid, itaconic acid, maleic acid, fumaric acid, $C_1$–$C_4$ alkyl half esters of maleic acid and $C_1$–$C_4$ alkyl half esters of fumaric acid, based on the total weight of monomer used to prepare the polymer, 25 to 97 weight percent of water, 0 to 40 weight percent of a propellant, an amount of a neutralizing agent effective to neutralize from 40 to 80 mole percent of the carboxyl groups present in the polymer, 0 to 15 weight percent of an emulsifier; and 0 to 35 weight percent of an organic solvent;

for a time period ranging from about 5 minutes to about 72 hours, at a temperature and a pressure ranging from standard temperature and pressure to a temperature of about 80° C. and a pressure of about 63 psi, thereby forming an aqueous, homogenous solution of the polymer in the water, wherein the water comprises greater than 50 weight percent of a solvent system which comprises the water and optionally the organic solvent, which solvent system is used in preparing the hair fixative composition.

9. The method of claim 8 wherein the polymer, the water and the neutralizing agent are combined and heated at a temperature ranging from about 70° C. to about 80° C. and for a period of time ranging from about 5 minutes to about 3 hours, thereby forming the aqueous, homogenous solution of the polymer.

10. The method of claim 8 wherein the polymer, the water and the neutralizing agent are heated to a temperature of from about 70° C. to about 80° C. until the aqueous, homogeneous solution is formed.

11. The composition of claim 9 wherein the aqueous, homogeneous solution of the polymer and from 2.5 to 35 weight percent of the propellant are combined under pressures ranging from about 40 psi to about 63 psi, thereby forming the hair fixative composition.

12. The composition of claim 8 wherein the polymer, the water, the neutralizing agent and 25 to 35 weight percent of the propellant are combined at standard temperature, under pressures ranging from about 40 psi to about 63 psi and for a period of time ranging from about 24 hours to about 72 hours, thereby forming the aqueous, acrylic, aerosol hair fixative composition.

13. The method of claim 8 comprising less than 25 weight percent of the organic solvent.

14. The method of claim 8 comprising from about 35 to about 65 weight percent of the water and less than 25 weight percent of the organic solvent.

* * * * *